United States Patent [19]
Woodle et al.

[11] 4,364,262
[45] Dec. 21, 1982

[54] CHARACTERIZATION FACTOR MONITOR

[75] Inventors: Robert A. Woodle, Nederland, Tex.; Ronald G. Gillespie, Old Tappan, N.J.

[73] Assignee: Texaco, Inc., White Plains, N.Y.

[21] Appl. No.: 247,654

[22] Filed: Mar. 26, 1981

[51] Int. Cl.³ .............................................. G01N 11/00
[52] U.S. Cl. ........................................ 73/53; 374/101
[58] Field of Search ................... 73/53, 61 R, 61.1 R, 73/61.3, 344, 36

[56] References Cited
U.S. PATENT DOCUMENTS

| | | | |
|---|---|---|---|
| 3,557,609 | 1/1971 | Woodle | 73/53 |
| 4,137,753 | 2/1979 | Woodle | 73/53 |
| 4,335,598 | 6/1982 | Woodle | 73/53 |

*Primary Examiner*—Steven L. Stephan
*Assistant Examiner*—Joseph W. Roskos
*Attorney, Agent, or Firm*—Carl G. Ries; Robert A. Kulason; Ronald G. Gillespie

[57] ABSTRACT

A characterization factor monitor samples oil and provides a signal K corresponding to the characterization factor of the oil. Signal K may be used as a control signal or may be displayed by conventional display means to an operator. The monitor includes a refractometer and a flash point analyzer sampling the oil and providing signals RIt and F corresponding to the refractive index of the oil and to the flash point in degrees F of the oil, respectively. A temperature sensor senses the temperature of the oil and provides a signal T representative thereof. An output circuit connected to the refractometer, to the flash point analyzer and to the temperature sensor provides signal K in accordance with signals F, RIt and T.

8 Claims, 2 Drawing Figures

CHARACTERIZATION FACTOR MONITOR

BACKGROUND OF THE INVENTION

Field of the Invention

The present invention relates to monitors in general and, more particularly, to a monitor for providing a signal corresponding to a characteristic of an oil.

SUMMARY OF THE INVENTION

A monitor samples oil and provides a signal corresponding to the characterization factor of the oil. The monitor includes a refractometer and a flash point analyzer which samples the oil and provides signals corresponding to the refractive index and the Cleveland open cup flash point temperature in degrees F of the oil. A sensor provides a signal corresponding to the sensed temperature of the oil. A network provides signal K in accordance with the signals from the refractometer, the flash point analyzer and the temperature sensor.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE INVENTION

The characterization factor, often referred to as the Watson K, is a useful, empirical tool for expressing by a single number the approximate relative paraffinicity of a petroleum fraction.

The magnitude of K provides a useful information about an oil fraction, including an indication of the type of crude from which a virgin oil was derived, or the type of processing that a refined oil may have received. The technical literature also includes descriptions of ways to use the Watson K factor to interrelate various physical properties of oils, including boil point temperature, molecular weight, hydrogen content and specific heat.

Therefore, it is extremely useful to continuously monitor the characterization factor of refinery processed streams of distinguish among products, and to detect changes that occur during processing. The characterization factor K can also be used as the basis for controlling various refinery operations.

Heretofore, the physical properties that have been used for estimating the Watson K factor of a particular oil fraction have mainly included the density, or specific gravity, in combination with viscosity, average boiling point, flash point or aniline point. It has now been discovered unexpectedly that the Watson K factor can be accurately determined from a combination of two properties not previously used together, namely, the flash point temperature and the refractive index.

Figure 1:
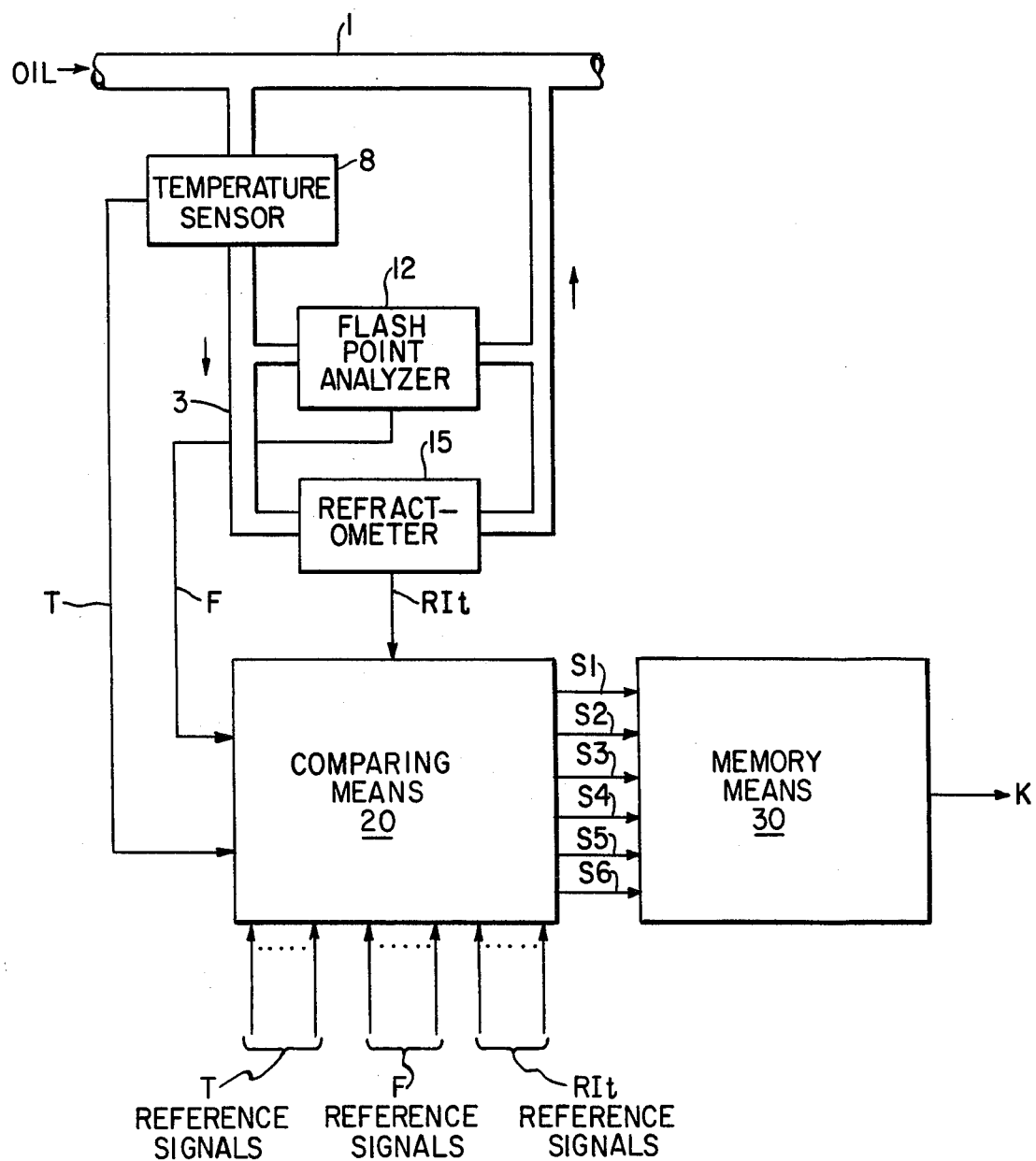
FIG. 1 is a simplified block diagram of a monitor constructed in accordance with the present invention for sampling oil and providing a signal corresponding to the characterization factor of the oil.

Referring to FIG. 1, oil flowing in a pipe 1 also flows through bypass pipes 3 and 4 as hereinafter explained, to return to the stream of oil in pipe 1. A temperature sensor 8 senses oil in line 3 and provides a signal T corresponding thereto. A conventional type flash point analyzer 12 samples the oil in line 3 and provides the sample oil to line 4. Analyzer 12 provides a signal F corresponding to the flash point temperature of the oil. A refractometer 15 also samples the oil and provides a signal RIt corresponding to the refractive index at temperature T of the sample oil. The sample oil from the refractometer 15 is also returned to line 4. Signals T, F and RIt are provided to comparing means 20 receiving temperature reference signals, flash point temperature reference signals and refractive index reference signals. Comparing means 20, through a comparison of signal T with the temperature reference signals, of signal F with the F reference signals and of signal RIt with the RIt reference signals, provides address signals S1 through S5 to memory means 30. Memory means 30 has stored within it different values for K for different combinations of F, T and RIt which have been determined from laboratory testing or other conventional methods. Signals S1 through S5 address memory means 30 and cause it to provide signal K corresponding to the Watson K factor of the oil flowing through pipe 1.

Figure 2:
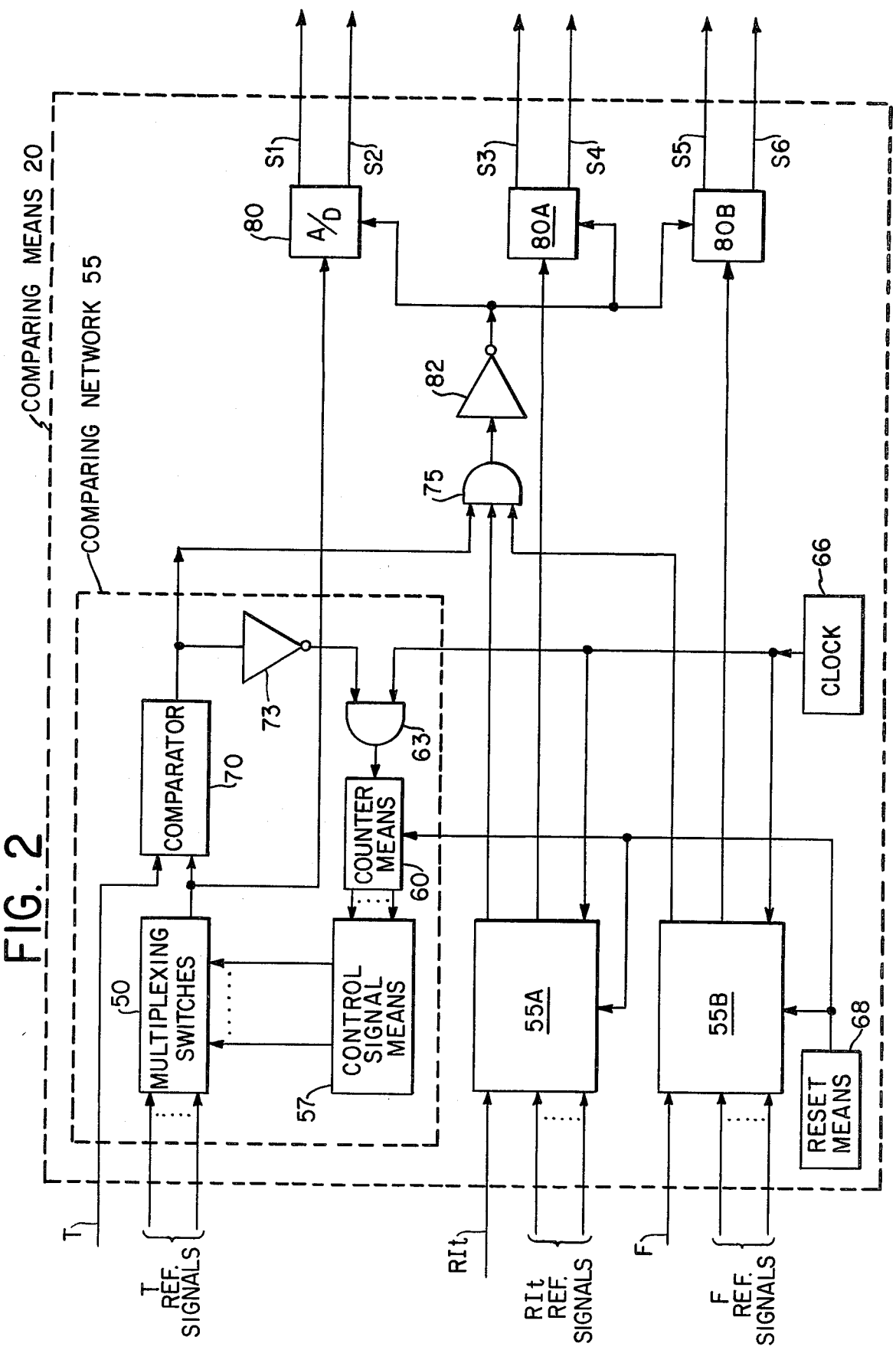
FIG. 2 is a detailed block diagram of the comparing means shown in FIG. 1.

Referring now to FIG. 2, temperature reference signals are provided to multiplexing switches 50 in a comparing network 55. Multiplexing switches are controlled by control signals provided by control signal means 57 in response to signals from counter means 60. Counter means 60 counts passed pulses from an AND gate 63 receiving clock pulses from a clock 66. Counter means 60 is also reset by a reset pulse from reset means 68 as hereinafter explained.

Signal T is provided to a comparator 70 which compares signal T with a multiplexed reference signal from multiplexing switches 50 and provides a comparison signal to an inverter 73 and to an AND gate 75. Inverter 73 provides its output to AND gate 63 to control the passage of clock pulses from clock 66 as hereinafter explained.

In operation, a comparison signal from comparator 70 is initially at a low logic level which is inverted to a high logic level signal by inverter 73 to enable AND gate 63 to pass the clock pulses from clock 66. As counter means 60 counts the passed clock pulses, its signals are decoded by control signal means 57 to provide control signals causing multiplexing switches 50 to sequentially pass the temperature reference signals to comparator 70. At some point in time, a multiplex temperature reference signal is greater than signal T which causes comparators 70 to provide the comparison signal at a high logic level which after inversion by inverter 73 disables AND gate 63 to prevent further counting by counter means 60. The reference signal from multiplexing switches 50 at this time represents the value of signal T and is provided to an analog-to-digital converter 80.

Similarly, signal RIt and RIt reference signals are provided to comparing network 55A. Elements having the same numerical designation but with an alpha suffix are constructed and operate in a similar manner as the element having the same numeric identification without a suffix. Comparing network 55A, when it has selected the correct RIt reference signal, provides the selected RIt reference signal to another analog-to-digital converter 80A and the comparison signal to AND gate 75.

Similarly, comparing network 55B processes signal T and T reference signals to provide a selected T reference signal to yet another analog-to-digital converter 80B and its comparison signal to AND gate 75. When all three parameter reference signals have been selected, the comparison signals from comparing networks 55, 55A and 55B are at high logic levels causing AND gate 75 to provide its output at a high logic level which, in turn, is inverted by an inverter 82 and provided to analog-to-digital converters 80, 80A and 80B. The changing of logic levels, from a high logic level to a low logic level, of the signal from inverter 82 causes analog-to-digital converters 80, 80A and 80B to convert the selected reference signals and provide corresponding digital signals S1 through S6.

The testing cycle is reinitiated by reset means 68 providing a reset pulse which resets the counter means 60 in each of the comparing networks 55, 55A and 55B, causing them to recycle. Reset means 68 may be just simply a manually operative switch receiving a voltage which, when activated, provides a reset pulse. It may be an automatic feature that is a counter receiving clock pulses from clock 66 and after a predetermined time interval automatically provides a reset pulse.

The present invention as hereinbefore stated is a monitor which provides a signal corresponding to the Watson K characterization factor of oil being monitored.

What is claimed is:

1. A monitor which provides a signal K corresponding to the characterization factor of oil, comprises:
    means for sampling the oil and providing signals F and RIt corresponding to the flash point temperature in degrees F and the refractive index of the oil, respectively,
    means for sensing the temperature of the oil and providing a signal T representative thereof, and
    output means connected to the sampling means and to the temperature sensing means for providing signal K in accordance with signals F, RIt and T.

2. A monitor as described in claim 1 in which the output means includes
    memory means for storing different values of K for different values of signals T, RIt and F, and
    control means connected to the sampling means and to the temperature sensing means and responsive to signals T, RIt and F for controlling the memory means to provide signal K in accordance with one of the stored values of K.

3. A monitor as described in claim 2 in which the control means includes:
    comparing means connected to the sampling means, to the temperature sensing means and to the memory means and receiving a plurality of temperature reference signals, a plurality of RIt reference signals and a plurality of F reference signals for providing address signals to the memory means in accordance with signals T, F and RIt, the temperature reference signals, the RIt reference signals and the F reference signals so as to control the memory means to provide signal K.

4. A monitor as described in claim 3 in which the comparing means includes:
    a first selection means connected to the temperature sensing means and receiving the plurality of temperature reference signals for providing a selected temperature reference signal in accordance with signal T,
    second selection means connected to the sampling means and receiving the plurality of F reference signals for providing a selected F reference signal in accordance with signal F,
    third selection means connected to the sampling means and receiving the plurality of RIt reference signals for providing a selected RIt reference signal in accordance with signal RIt, and
    address signal means connected to all the selection means for providing the address signals to the memory means in accordance with the selected temperature reference signal, the selected F reference signal and the selected RIt reference signal.

5. A monitor as described in claim 4 in which the comparing means further comprises a clock providing clock pulses and in which each selection means includes an AND gate receiving the clock pulses from the clock means, counter means connected to the AND gate counting pulses passed by said AND gate, multiplexing means receiving the reference signals and responsive to the counting by the counter means for sequentially passing the reference signals, comparator means connected to the multiplexing means and to a corresponding sensing means or sampling means for comparing the signal from the corresponding sensing means or sampling means with the reference signal provided by the multiplexing means to provide a first comparison signal which is of one amplitude when the signal from the sensing means or sampling means is greater than the reference signal provided by the multiplexing means and of another amplitude when the signal from the sensing means or sampling means is equal to or less than the reference signal provided by the multiplexing means, and an inverter connecting the comparator means to the AND gate for enabling the AND gate to pass the clock pulses when the comparison signal is of the one amplitude and for disabling the AND gate so as to block the clock pulses when the comparison signal is of the other amplitude.

6. A monitor as described in claim 5 in which the address means includes:
    a second AND gate connected to all the comparator means,
    a second inverter connected to the second AND gate, and
    a plurality of analog-to-digital converters, each analog-to-digital converter being connected to the multiplexing means in a different selection means and to the second inverter so that when all three comparison signals are at the other amplitude, the second AND gate provides an output of a similar amplitude which is inverted by the second inverter to cause the analog-to-digital converters to convert the selected reference signals to corresponding digital signals which are provided as the address signals.

7. A monitor as described in claim 6 further comprising:
    reset means connected to the counter means in each selection means for manually resetting the counter means.

8. A monitor as described in claim 6 further comprising:
    reset means connected to the counter means in each selection means for periodically resetting the counter means so as to recycle the operation of the monitor.

* * * * *